United States Patent
Dorsch et al.

(10) Patent No.: US 9,079,910 B2
(45) Date of Patent: Jul. 14, 2015

(54) 5-(1,2,3-TRIAZOL-4-YL)-7H-PYRROLO [2,3-D]PYRIMIDINE DERIVATIVES

(75) Inventors: Dieter Dorsch, Ober-Ramstadt (DE); Margarita Wucherer-Plietker, Messel (DE); Thomas J. J. Mueller, Duesseldorf (DE); Eugen Merkul, Duesseldorf (DE)

(73) Assignee: Merck Patent GmbH, Darmstadt (DE)

( * ) Notice: Subject to any disclaimer, the term of this patent is extended or adjusted under 35 U.S.C. 154(b) by 71 days.

(21) Appl. No.: 13/978,545

(22) PCT Filed: Dec. 15, 2011

(86) PCT No.: PCT/EP2011/006354
§ 371 (c)(1),
(2), (4) Date: Jul. 8, 2013

(87) PCT Pub. No.: WO2012/095142
PCT Pub. Date: Jul. 19, 2012

(65) Prior Publication Data
US 2013/0289017 A1    Oct. 31, 2013

(30) Foreign Application Priority Data
Jan. 12, 2011  (DE) .......................... 10 2011 008 352

(51) Int. Cl.
*C07D 487/04* (2006.01)
*C07D 487/02* (2006.01)
*A61K 31/519* (2006.01)
*A61K 45/06* (2006.01)

(52) U.S. Cl.
CPC ............ *C07D 487/04* (2013.01); *A61K 31/519* (2013.01); *A61K 45/06* (2013.01); *C07D 487/02* (2013.01)

(58) Field of Classification Search
None
See application file for complete search history.

(56) References Cited

U.S. PATENT DOCUMENTS

2012/0053178 A1    3/2012  Dorsch et al.

FOREIGN PATENT DOCUMENTS

WO    2010127754 A1    11/2010

OTHER PUBLICATIONS

Merkul, et. al., Organic & Biomolecular Chemistry (2011), 9(14), 5129-5136.*
International Search Report from PCT/EP2011/006354 dated Apr. 3, 2012.

* cited by examiner

*Primary Examiner* — Jeffrey H Murray
(74) *Attorney, Agent, or Firm* — Millen, White, Zelano & Branigan, P.C.

(57) ABSTRACT

Compounds of the formula (I), in which $R^1$, $R^2$, $R^{2a}$ and $R^3$ have the meanings indicated in Claim 1, are inhibitors of PDK1 and cell proliferation/cell vitality and can be employed for the treatment of tumors.

13 Claims, No Drawings

5-(1,2,3-TRIAZOL-4-YL)-7H-PYRROLO[2,3-D]PYRIMIDINE DERIVATIVES

The invention relates to compounds of the formula I

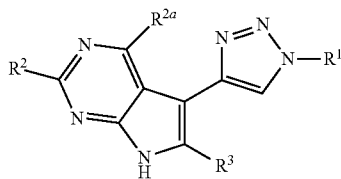

in which
$R^1$ denotes A, —$C(R^3)(R^4)$—Ar, —$C(R^3)(R^4)$-Het or —$C(R^3)(R^4)$-Cyc,
$R^2$, $R^{2a}$ each, independently of one another, denote H, A, Hal, CN, —$[C(R^3)_2]_n$—Ar', —$[C(R^3)_2]_n$-Het', —$[C(R^3)_2]_n$-Cyc, $OR^3$ or $N(R^3)_2$,
$R^3$ denotes H or A,
$R^4$ denotes H, A, —$[C(R^3)_2]_m OR^3$, —$[C(R^3)_2]_m N(R^3)_2$ or —$[C(R^3)_2]_m Het^1$,
A denotes unbranched or branched alkyl having 1-6C atoms, in which one or two non-adjacent $CH_2$ groups may be replaced by O, N and/or S atoms and/or by —CH=CH— groups and/or, in addition, 1-7H atoms may be replaced by F,
Cyc denotes cycloalkyl having 3, 4, 5, 6 or 7C atoms,
Ar denotes phenyl which is unsubstituted or mono-, di- or trisubstituted by Hal, A, $OR^3$, $N(R^3)_2$, $NO_2$, CN, $COOR^3$, $CON(R^3)_2$, $NR^3COA$, $NR^3SO_2A$, $COR^3$, $SO_2N(R^3)_2$ and/or $S(O)_nA$,
Ar' denotes phenyl which is unsubstituted or mono-, di- or trisubstituted by Hal, A, $OR^3$, $N(R^3)_2$, $SR^3$, $NO_2$, CN, $COOR^3$, $CON(R^3)_2$, $NR^3COA$, $NR^3SO_2A$, $SO_2N(R^3)_2$, $S(O)_mA$, CO-$Het^1$, $Het^1$, $[C(R^3)_2]_n$—$N(R^3)_2$, $[C(R^3)_2]_n Het^1$, $O[C(R^3)_2]_n N(R^3)_2$, $O[C(R^3)_2]_n Het^1$, NHCOOA, $NHCON(R^3)_2$, $NHCOO[C(R^3)_2]_n N(R^3)_2$, $NHCOO[C(R^3)_2]_n Het^1$, $NHCONH[C(R^3)_2]_n N(R^3)_2$, $NHCONH[C(R^3)_2]_n Het^1$, $OCONH[C(R^3)_2]_n N(R^3)_2$, $OCONH[C(R^3)_2]_n Het^1$, CO-$Het^1$, CHO and/or COA,
Het denotes a mono- or bicyclic saturated, unsaturated or aromatic heterocycle having 1 to 4 N, and/or O and/or S atoms which is unsubstituted or mono- or disubstituted by Hal, A, $OR^3$, $N(R^3)_2$, $NO_2$, CN, $COOR^3$, $CON(R^3)_2$, $NR^3COA$, $NR^3SO_2A$, $COR^3$, $SO_2NR^3$ and/or $S(O)_nA$,
Het' denotes a mono-, bi- or tricyclic saturated, unsaturated or aromatic heterocycle having 1 to 4 N, O and/or S atoms, which is unsubstituted or may be mono- or disubstituted by Hal, A, $OR^3$, $N(R^3)_2$, $SR^3$, $NO_2$, CN, $COOR^3$, $CON(R^3)_2$, $NR^3COA$, $NR^3SO_2A$, $SO_2N(R^3)_2$, $S(O)_mA$, CO-$Het^1$, $Het^1$, $[C(R^3)_2]_n N(R^3)_2$, $[C(R^3)_2]_n Het^1$, $O[C(R^3)_2]_n N(R^3)_2$, $O[C(R^3)_2]_n Het^1$, NHCOOA, $NHCON(R^3)_2$, $NHCOO[C(R^3)_2]_n N(R^3)_2$, $NHCOO[C(R^3)_2]_n Het^1$, $NHCONH[C(R^3)_2]_n N(R^3)_2$, $NHCONH[C(R^3)_2]_n Het^1$, $OCONH[C(R^3)_2]_n N(R^3)_2$, $OCONH[C(R^3)_2]_n Het^1$, CO-$Het^1$, CHO, COA, =S, =NH, =NA and/or =O (carbonyl oxygen),
$Het^1$ denotes a monocyclic saturated heterocycle having 1 to 2 N and/or O atoms, which may be mono- or disubstituted by A, OA, OH, Hal and/or =O (carbonyl oxygen),
Hal denotes F, Cl, Br or I
n denotes 0, 1 or 2
m denotes 1 or 2,
and pharmaceutically usable salts, tautomers and stereoisomers thereof, including mixtures thereof in all ratios.

The compounds of the formula I according to the invention also include the pharmaceutically usable derivatives and solvates thereof.

The invention was based on the object of finding novel compounds having valuable properties, in particular those which can be used for the preparation of medicaments.

It has been found that the compounds of the formula I and salts and/or solvates thereof have very valuable pharmacological properties while being well tolerated.

In particular, they exhibit a cell proliferation/cell vitality-inhibiting action as antagonists or agonists. The compounds according to the invention can therefore be used for the combating and/or treatment of tumours, tumour growth and/or tumour metastases.

The antiproliferative action can be tested in a proliferation assay/vitality assay.

The compounds according to the invention inhibit the proliferation of cancer cells, for example the proliferation of cell lines A2780 and HCT116.

3-(1,2,3-Triazol-4-yl)pyrrolo[2,3-b]pyridine derivatives are described as PDK1 inhibitors in WO 2010/127754 A1.

Accordingly, the compounds according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compounds are furthermore useful in the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynaecological cancer, thyroid cancer, lymphomas, chronic leukaemia and acute leukaemia. In particular, cancer-like cell growth is a disease which represents a target of the present invention. The present invention therefore relates to compounds according to the invention as medicaments and/or medicament active compounds in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an antiproliferative action. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, perianastomatic prosthetic restenosis, restenosis after angioplasty or stent placement, and the like.

The compounds of the formula I, also act as regulators, modulators or inhibitors of protein kinases, in particular of the serine/threonine kinase type, which include, inter alia, phosphoinositide-dependent kinase 1 (PDK1). The compounds according to the invention exhibit a certain action in the inhibition of the serine/threonine kinases PDK1, IKK and TBK1.

PDK1 phosphorylates and activates a sub-group of the AGC protein kinase family, comprising PKB, SGK, S6K and PKC isoforms. These kinases are involved in the PI3K signal transduction pathway and control basic cellular functions, such as survival, growth and differentiation. PDK1 is thus an important regulator of diverse metabolic, proliferative and life-sustaining effects.

WO 2008/079988 A2 describes quinazoline derivatives as PDK1 inhibitors for combating cancer.

WO 2008/112217 A1 describes benzonaphthyridine derivatives as PDK1 inhibitors for combating cancer.

Pyridinonyl derivatives are known as PDK1 inhibitors for combating cancer from WO 2008/005457.

Pyrrolopyridine kinase modulators for combating cancer are described in WO WO 2008/124849.

WO 2006/106326 A1 and WO 2008/156726 A1 describe other heterocyclic compounds as PDK1 inhibitors for combating cancer.

WO 2009/054941 A1 describes pyrrolopyridine derivatives as PDK1 inhibitors for combating cancer.

IKKε and TBK1 are serine/threonine kinases which are highly homologous to one another and to other IkB kinases. The two kinases play an integral role in the innate immune system. Double-stranded RNA viruses are recognised by the Toll-like receptors 3 and 4 and the RNA helicases RIG-I and MDA-5 and result in activation of the TRIF-TBK1/IKKε-IRF3 signalling cascade, which results in a type I interferon response.

In 2007, Boehm et al. described IKKε as a novel breast cancer oncogene [J. S. Boehm et al., Cell 129, 1065-1079, 2007]. 354 kinases were investigated with respect to their ability to recapitulate the Ras-transforming phenotype together with an activated form of the MAPK kinase Mek. IKKε was identified here as a cooperative oncogene.

In addition, the authors were able to show that IKBKE is amplified and overexpressed in numerous breast cancer cell lines and tumour samples. The reduction in gene expression by means of RNA interference in breast cancer cells induces apoptosis and impairs the proliferation thereof. Eddy et al. obtained similar findings in 2005, which underlines the importance of IKKε in breast cancer diseases [S. F. Eddy et al., Cancer Res. 2005; 65 (24), 11375-11383].

A protumorigenic effect of TBK1 was reported for the first time in 2006. In a screening of a gene library comprising 251,000 cDNA, Korherr et al. identified precisely three genes, TRIF, TBK1 and IRF3, which are typically involved in the innate immune defence as proangiogenic factors [C. Korherr et al., PNAS, 103, 4240-4245, 2006]. In 2006, Chien et al. [Y. Chien et al., Cell 127, 157-170, 2006] published that TBK1−/− cells can only be transformed to a limited extent using oncogenic Ras, which suggests an involvement of TBK1 in the Ras-mediated transformation. Furthermore, they were able to show that an RNAi-mediated knockdown of TBK1 triggers apoptosis in MCF-7 and Panc-1 cells. Barbie et al. recently published that TBK1 is of essential importance in numerous cancer cell lines with mutated K-Ras, which suggests that TBK1 intervention could be of therapeutic importance in corresponding tumours [D. A. Barbie et al., Nature Letters 1-5, 2009].

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase, or the generation of an activity level which can be correlated with a cell proliferation disease (i.e. the severity of one or more symptoms of the cell proliferation disease increases with increasing kinase level). The bioavailability of a protein kinase may also be influenced by the presence or absence of a set of binding proteins of this kinase.

The most important types of cancer that can be treated using a compound according to the invention include colorectal cancer, small-cell lung cancer, non-small-cell lung cancer, multiple myeloma as well as renal cell carcinoma and endometrium carcinoma, particularly also types of cancer in which PTEN is mutated, inter alia breast cancer, prostate cancer and glioblastoma.

In addition, the compounds according to the invention can be used to achieve additive or synergistic effects in certain existing cancer chemotherapies and radiotherapies and/or to restore the efficacy of certain existing cancer chemotherapies and radiotherapies.

Compounds of the formula I are also taken to mean the hydrates and solvates of these compounds, furthermore pharmaceutically usable derivatives.

The invention also relates to the optically active forms (stereoisomers), salts, the enantiomers, the racemates, the diastereomers and the hydrates and solvates of these compounds. Solvate of the compounds are taken to mean adductions of inert solvent molecules onto the compounds which form owing to their mutual attractive force. Solvate are, for example, mono- or dihydrates or alcoholates. Compounds of the formula I are of course also taken to mean the solvates of the salts of the compounds according to the invention.

Pharmaceutically usable derivatives are taken to mean, for example, the salts of the compounds according to the invention and also so-called prodrug compounds. Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I and pharmaceutically usable salts, tautomers and stereoisomers thereof, characterised in that the indole-protecting group is cleaved off from a compound of the formula II

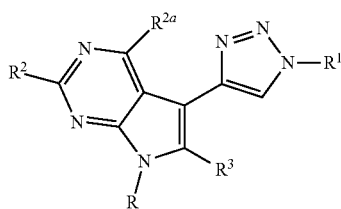

in which $R^1$, $R^2$, $R^{2a}$ and $R^3$ have the meanings indicated in Claim 1, and R denotes an indole-protecting group,
and/or a base or acid of the formula I is converted into one of its salts.

Above and below, the radicals $R^1$, $R^2$, $R^{2a}$ and $R^3$ have the meanings indicated for the formula I, unless expressly indicated otherwise.

A denotes alkyl, is unbranched (linear) or branched, and has 1, 2, 3, 4, 5, 6, 7, 8, 9 or 10C atoms. A preferably denotes methyl, furthermore ethyl, propyl, isopropyl, butyl, isobutyl, sec-butyl or tert-butyl, furthermore also pentyl, 1-, 2- or 3-methyl-butyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

One or two non-adjacent CH and/or $CH_2$ groups in A may also be replaced by N, O and/or S atoms and/or by —CH═CH— groups. A thus also denotes, for example, 2-methoxyethyl or 2-hydroxyethyl.

A furthermore preferably denotes unbranched or branched alkyl having 1-6C atoms, in which one or two non-adjacent $CH_2$ groups may be replaced by an O, N and/or S atom and/or, in addition, 1-7H atoms may be replaced by F.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-fluorophenyl, o-, m- or p-bromophenyl, o-, m- or p-chlorophenyl, o-, m- or p-hydroxyphenyl, o-, m- or p-methoxyphenyl, o-, m- or p-methylsulfonylphenyl, o-, m- or p-nitrophenyl, o-, m- or p-aminophenyl, o-, m- or p-methylaminophenyl, o-, m- or p-dimethylaminophenyl, o-, m- or p-aminosulfonylphenyl, o-, m- or p-methyl-aminosulfonylphenyl, o-, m- or p-aminocarbonylphenyl, o-, m- or p-carboxy-phenyl, o-, m- or p-methoxycarbonylphenyl, o-, m- or p-ethoxycarbonylphenyl, o-, m- or p-acetylphenyl, o-, m- or p-formylphenyl, o-, m- or p-cyanophenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, p-iodophenyl, 4-fluoro-3-chlorophenyl, 2-fluoro-4-bromophenyl, 2,5-difluoro-4-bromophenyl or 2,5-dimethyl-4-chlorophenyl.

Ar preferably denotes phenyl which is unsubstituted or mono- or disubstituted by Hal and/or A.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Unsubstituted Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy) phenyl, 2,3-dihydro-benzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het furthermore preferably denotes a mono- or bicyclic aromatic, unsaturated or saturated heterocycle having 1 to 4 N, and/or O and/or S atoms which is unsubstituted or mono- or disubstituted by A.

Het very particularly preferably denotes furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, indolyl, isoindolyl, benzimidazolyl, indazolyl, quinolyl, 1,3-benzodioxolyl, azetidinyl, pyrrolidinyl, tetrahydroimidazolyl, tetrahydropyrazolyl, piperidinyl, morpholinyl, piperazinyl, oxazolidinyl or isoxazolidinyl.

Het particularly preferably denotes azetidinyl, pyrrolidinyl, tetrahydroimidazolyl, tetrahydropyrazolyl, piperidinyl, morpholinyl, piperazinyl, oxazolidinyl or isoxazolidinyl.

Irrespective of further substitutions, Het' preferably has the meanings as indicated for Het.

Het' furthermore preferably denotes a mono- or bicyclic aromatic heterocycle having 1 to 4 N, O and/or S atoms which is unsubstituted or may be mono- or disubstituted by A and/or $[C(R^3)_2]_n Het^1$.

Het' very particularly preferably denotes furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, indolyl, isoindolyl, benzimidazolyl, indazolyl, quinolyl or 1,3-benzodioxolyl, each of which is unsubstituted or mono- or disubstituted by A and/or $[C(R^3)_2]_n Het^1$.

$Het^1$ preferably denotes a monocyclic saturated heterocycle having 1 to 2 N and/or O atoms, which may be mono- or disubstituted by A.

$Het^1$ very particularly preferably denotes azetidinyl, pyrrolidinyl, tetrahydroimidazolyl, tetrahydropyrazolyl, piperidinyl, morpholinyl, piperazinyl, oxazolidinyl or isoxazolidinyl, each of which is unsubstituted or mono- or disubstituted by A.

$R^1$ preferably denotes —$C(R^3)(R^4)$—Ar.

$R^2$, $R^{2a}$ preferably denote, in each case independently of one another, H or A.

$R^3$ preferably denotes H, methyl, ethyl, propyl or butyl.

$R^4$ preferably denotes H, —$[C(R^3)_2]_m N(R^3)_2$ or —$[C(R^3)_2]_m Het^1$.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to II, which conform to the formula I and in which the radicals not designated in greater detail have the meaning indicated for the formula I, but in which

| | | |
|---|---|---|
| in Ia | $R^1$ | denotes —$C(R^3)(R^4)$—Ar; |
| in Ib | $R^2$, $R^a$ | each, independently of one another, denote H or A; |
| in Ic | $R^4$ | denotes H, —$[C(R^3)_2]_m N(R^3)_2$ or —$[C(R^3)_2]_m Het^1$; |
| in Id | A | denotes unbranched or branched alkyl having 1-6 C atoms, in which one or two non-adjacent $CH_2$ groups may be replaced by an O, N and/or S atom and/or, in addition, 1-7 H atoms may be replaced by F; |
| in Ie | Ar | denotes phenyl which is unsubstituted or mono- or disubstituted by Hal and/or A; |
| in If | Het | denotes azetidinyl, pyrrolidinyl, tetrahydroimidazolyl, tetrahydropyrazolyl, piperidinyl, morpholinyl, piperazinyl, oxazolidinyl or isoxazolidinyl; |
| in Ig | Het' | denotes a mono- or bicyclic aromatic heterocycle having 1 to 4 N, O and/or S atoms, which is unsubstituted or may be mono- or disubstituted by A and/or $[C(R^3)_2]_n Het^1$; |
| in Ih | $Het^1$ | denotes a monocyclic saturated heterocycle having 1 to 2N and/or O atoms, which may be mono- or disubstituted by A; |
| in Ii | Het | denotes furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, indolyl, isoindolyl, benzimidazolyl, indazolyl, quinolyl, 1,3-benzodioxolyl or azetidinyl, pyrrolidinyl, tetrahydroimidazolyl, tetrahydropyrazolyl, piperidinyl, morpholinyl, piperazinyl, oxazolidinyl or isoxazolidinyl; |
| in Ij | Het' | denotes furyl, thienyl, pyrrolyl, imidazolyl, pyrazolyl, oxazolyl, isoxazolyl, thiazolyl, pyridyl, pyrimidinyl, triazolyl, tetrazolyl, thiadiazole, pyridazinyl, pyrazinyl, indolyl, isoindolyl, benzimidazolyl, indazolyl, quinolyl or 1,3-benzodioxolyl, each of which is unsubstituted or mono- or disubstituted by A and/or $[C(R^3)_2]_n Het^1$; |

| | | |
|---|---|---|
| in Ik | Het¹ | denotes azetidinyl, pyrrolidinyl, tetrahydroimidazolyl, tetrahydropyrazolyl, piperidinyl, morpholinyl, piperazinyl, oxazolidinyl or isoxazolidinyl, each of which is unsubstituted or mono- or disubstituted by A; |
| in Il | R¹ | denotes —C(R³)(R⁴)—Ar, |
| | R², R²ᵃ | each, independently of one another, denote H or A, |
| | R³ | denotes H or A, |
| | R⁴ | denotes H, —[C(R³)₂]ₘN(R³)₂ or —[C(R³)₂]ₘHet¹; |
| | A | denotes unbranched or branched alkyl having 1-6 C atoms, in which one or two non-adjacent CH₂ groups may be replaced by an O, N and/or S atom and/or, in addition, 1-7 H atoms may be replaced by F, |
| | Ar | denotes phenyl which is unsubstituted or mono- or disubstituted by Hal and/or A, |
| | Het¹ | denotes a monocyclic saturated heterocycle having 1 to 2N and/or O atoms, which may be once or twice by A, |
| | Hal | denotes F, Cl, Br or I, |
| | m | denotes 1 or 2, | and pharmaceutically usable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

Compounds of the formula I can preferably be obtained by cleaving the indole-protecting group off from compounds of the formula II.

The reaction is carried out in an inert solvent and is generally carried out in the presence of an alkali or alkaline-earth metal hydroxide, carbonate or bicarbonate or another salt of a weak acid of the alkali or alkaline-earth metals, preferably of potassium, sodium, calcium or caesium.

Depending on the conditions used, the reaction time is between a few minutes and 14 days, the reaction temperature is between about −15° and 150°, normally between 10° and 100°, particularly preferably between 15° and 80° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to alcohols, such as, for example, methanol.

Preferred indole-protecting groups are, for example, sulfonyl-protecting groups, such as tosyl or mesyl, furthermore protecting groups such as, for example, BOC.

Compounds of the formula II can preferably be obtained by reacting a compound of the formula III

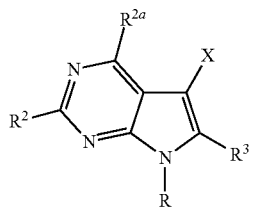

III in which
R², R²ᵃ and R³ have the meanings indicated in Claim 1,
R denotes an indole-protecting group,
X denotes Cl, Br, I or OTf,
with trimethylacetylene and a transition-metal catalyst in a Sonogashira reaction, preferably copper-catalysed [Lit.: Rafael Chinchilla and Carmen Nájera, Chem. Rev. 2007, 107, 874-922] and subsequently reacting with a compound of the formula IV

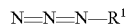    IV in which R¹ has the meaning indicated in Claim 1, in an azide-alkyne cycloaddition [Lit.: Morten Meldal and Christian Wenzel Tornøe, Chem. Rev., 2008, 108 (8), 2952-3015].

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogen-phosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound of the formula I in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The invention furthermore relates to medicaments comprising at least one compound of the formula I and/or pharmaceutically usable salts, tautomers and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsiloncaprolactone, polyhydroxybutyric acid, polyorthoesters, polyacetals, polydihydroxypyrans, polycyanoacrylates and crosslinked or amphipathic block co-polymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3 (6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable salts and stereoisomers thereof, including mixtures thereof in all ratios, and at least one further medicament active compound.

The invention also relates to a set (kit) consisting of separate packs of (a) an effective amount of a compound of the formula I and/or pharmaceutically usable salts and stereoisomers thereof, including mixtures thereof in all ratios, and (b) an effective amount of a further medicament active compound.

The set comprises suitable containers, such as boxes, individual bottles, bags or ampoules. The set may, for example, comprise separate ampoules, each containing an effective amount of a compound of the formula I and/or pharmaceutically usable salts and stereoisomers thereof, including mixtures thereof in all ratios, and an effective amount of a further medicament active compound in dissolved or lyophilised form.

Use

The present compounds are suitable as pharmaceutical active compounds for mammals, especially for humans, in the treatment and control of cancer diseases.

The present invention encompasses the use of the compounds of the formula I and/or physiologically acceptable salts, tautomers and stereoisomers thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

Also encompassed is the use of the compounds of the formula I and/or physiologically acceptable salts, tautomers and stereoisomers thereof for the preparation of a medicament for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

The compounds of the formula I may also be administered at the same time as other well-known therapeutic agents that are selected for their particular usefulness against the condition that is being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors. The present compounds are particularly suitable for administration at the same time as radiotherapy. "Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)-ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide. "Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)-mu-[diamineplatinum(II)]bis-[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H, 15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-amino-ethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and €-oligonucleotides such as G3139, ODN698, RVASKRAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine,N-[5-(2,3-dihydrobenzofuryl)sulfonyl]-N'-(3,4-dichloro-phenyl)urea, N6-[4-deoxy-4-[N2-[2€,4€-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Evidence of the Action of Pharmacological Inhibitors on the Proliferation/Vitality of Tumour Cells In Vitro 1.0 Background In the present experiment description, the inhibition of tumour cell proliferation/tumour cell vitality by active compounds is described.

The cells are sown in a suitable cell density in microtitre plates (96-well format) and the test substances are added in the form of a concentration series. After four further days of cultivation in serum-containing medium, the tumour cell proliferation/tumour cell vitality can be determined by means of an Alamar Blue test system.

2.0 Experimental Procedure 2.1 Cell Culture

For example commercially available colon carcinoma cell lines, ovary cell lines, prostate cell lines or breast cell lines, etc.

The cells are cultivated in medium. At intervals of several days, the cells are detached from the culture dishes with the aid of trypsin solution and sown in suitable dilution in fresh medium. The cells are cultivated at 37° Celsius and 10% $CO_2$.

2.2. Sowing of the Cells

A defined number of cells (for example 2000 cells) per culture/well in a volume of 180 µl of culture medium are sown in microtitre plates (96 well cell-culture plates) using a multichannel pipette. The cells are subsequently cultivated in a CO2 incubator (37° C. and 10% CO2).

2.3. Addition of the Test Substances

The test substances are dissolved, for example, in DMSO and subsequently employed in corresponding concentration (if desired in a dilution series) in the cell culture medium. The dilution steps can be adapted depending on the efficiency of the active compounds and the desired spread of the concentrations. Cell culture medium is added to the test substances in corresponding concentrations. The addition of the test substances to the cells can take place on the same day as the sowing of the cells. To this end, in each case 20 µl of substance solution from the predilution plate are added to the cultures/wells. The cells are cultivated for a further 4 days at 37° Celsius and 10% $CO_2$.

2.4. Measurement of the Colour Reaction

In each case, 20 µl of Alamar Blue reagent are added per well, and the microtitre plates are incubated, for example, for a further seven hours in a CO2 incubator (at 37° C. and 10% CO2). The plates are measured in a reader with a fluorescence filter at a wavelength of 540 nm. The plates can be shaken gently immediately before the measurement.

3. Evaluation

The absorbance value of the medium control (no cells and test substances used) is subtracted from all other absorbance values. The controls (cells without test substance) are set equal to 100 percent, and all other absorbance values are set in relation thereto (for example in % of control):

Calculation:

$$100 * \frac{\text{(value with cells and test substance} - \text{value of medium control)}}{\text{(value with cells} - \text{value of medium control)}}$$

$IC_{50}$ values (50% inhibition) are determined with the aid of statistics programs, such as, for example, RS1.

$IC_{50}$ data of compounds according to the invention are indicated in Table 1.

4.0 Test for the Inhibition of PDK1

The experimental batches are carried out in a flashplate system with 384 wells/microtitration plate.

In each case, the PDK1 sample $His_6$-PDK1(1-50)(3.4 nM), the PDK1 substrate biotin-bA-bA-KTFCGTPEYLAPEVR-REPRILSEEEQEMFRDFDYIADWC (400 nM), 4 µM ATP (with 0.2 µCi of $^{33}$P-ATP/well) and the test substance in 50 µl of conventional experimental solution per well are incubated at 30° C. for 60 min. The test substances are employed in corresponding concentrations (if desired in a dilution series). The control is carried out without test substance. The reaction is stopped using standard methods and washed. The activity of the kinase is measured via the incorporated radioactivity in top count. In order to determine the non-specific kinase reaction (blank value), the experimental batches are carried out in the presence of 100 nM staurosporine.

5.0 Evaluation

The radioactivity (decompositions per minute) of the blank value (no use of test substance in the presence of staurosporine) is subtracted from all other radioactivity values. The controls (kinase activity without test substance) are set equal to 100 percent and all other radioactivity values (after subtracting the blank value) are expressed set in relation thereto (for example in % of the control).

Calculation:

$$100 * \frac{\text{(value of the kinase activity with test substance} - \text{blank value)}}{\text{(value of the control} - \text{blank value)}} = \% \text{ of the control}$$

$IC_{50}$ values (50% inhibition) are determined with the aid of statistics programmes, such as, for example, RS1. $IC_{50}$ data of compounds according to the invention are indicated in Table 1.

| Material | Order No. | Manufacturer |
| --- | --- | --- |
| Microtitre plates for cell culture (Nunclon Surface 96-well plate) | 167008 | Nunc |
| DMEM | P04-03550 | Pan Biotech |
| PBS (10x) Dulbecco | 14200-067 | Gibco |
| 96-well plates (polypropylene) | 267334 | Nunc |
| AlamarBlue ™ | BUF012B | Serotec |
| FCS | 1302 | Pan Biotech GmbH |
| Trypsin/EDTA solution 10x | L 2153 | Biochrom AG |
| 75 $cm^2$ culture bottles | 353136 | BD Falcon |
| A2780 | 93112519 | ECACC |
| Colo205 | CCL222 | ATCC |
| MCF7 | HTB22 | ATCC |
| PC3 | CRL-1435 | ATCC |
| 384-well flash plates | SMP410A001PK | Perkin Elmer |

IKK—Kinase Test (IKKepsilon)

The kinase assay is performed as 384-well flashplate assay. 1 nM IKK, 800 nM biotinylated I B (19-42) peptide (biotin-C6-C6-GLKKERLLDDRHDSGLDSMKDEE) and 10 µM ATP (with 0.3 µCi of $^{33}$P-ATP/well) are incubated in a total volume of 50 µl (10 mM MOPS, 10 mM magnesium acetate, 0.1 mM EGTA, 1 mM dithiothreitol, 0.02% of Brij35, 0.1% of BSA, 0.1% of BioStab, pH 7.5) with or without test substance at 30° C. for 120 min. The reaction is stopped using 25 µl of 200 mM EDTA solution, filtered off with suction after 30 min at room temperature, and the wells are washed 3 times with 100 µl of 0.9% NaCl solution. The non-specific proportion of the kinase reaction (blank) is determined using 3 µM BX-795. Radioactivity is measured in the Topcount. $IC_{50}$ values are calculated using RS1.

TBK1—Kinase Test

The kinase assay is performed as 384-well flashplate assay. 0.6 nM TANK binding kinase (TBK1), 800 nM biotinylated MELK-derived peptide (biotin-Ah-Ah-AKP-KGNKDYHLQTCCGSLAYRRR) and 10 µM ATP (with 0.25 µCi of $^{33}$P-ATP/well) are incubated in a total volume of 50 µl (10 mM MOPS, 10 mM magnesium acetate, 0.1 mM EGTA, 1 mM DTT, 0.02% of Brij35, 0.1% of BSA, pH 7.5) with or without test substance at 30° C. for 120 min. The reaction is stopped using 25 µl of 200 mM EDTA solution, filtered off with suction after 30 min at room temperature, and the wells are washed 3 times with 100 µl of 0.9% NaCl solution. The non-specific proportion of the kinase reaction (blank) is determined using 100 nM staurosporine. Radioactivity is measured in the Topcount. $IC_{50}$ values are calculated using RS1.

HPLC/MS Method:

Column: Chromolith SpeedROD RP-18e, 50×4.6 mm$^2$

Gradient: A:B=96:4 to 0:100

Flow rate: 2.4 ml/min

Eluent A: water+0.05% of formic acid

Eluent B: acetonitrile+0.04% of formic acid

Wavelength: 220 nm

Mass spectroscopy: positive mode

Example 1

Preparation of 5-(1-benzyl-1H-1,2,3-triazol-4-yl)-4-(2-methoxyethoxy)-7H-pyrrolo[2,3-d]pyrimidine ("A1")

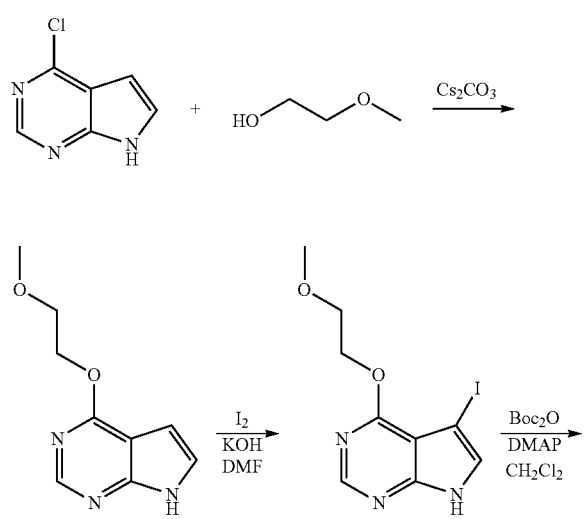

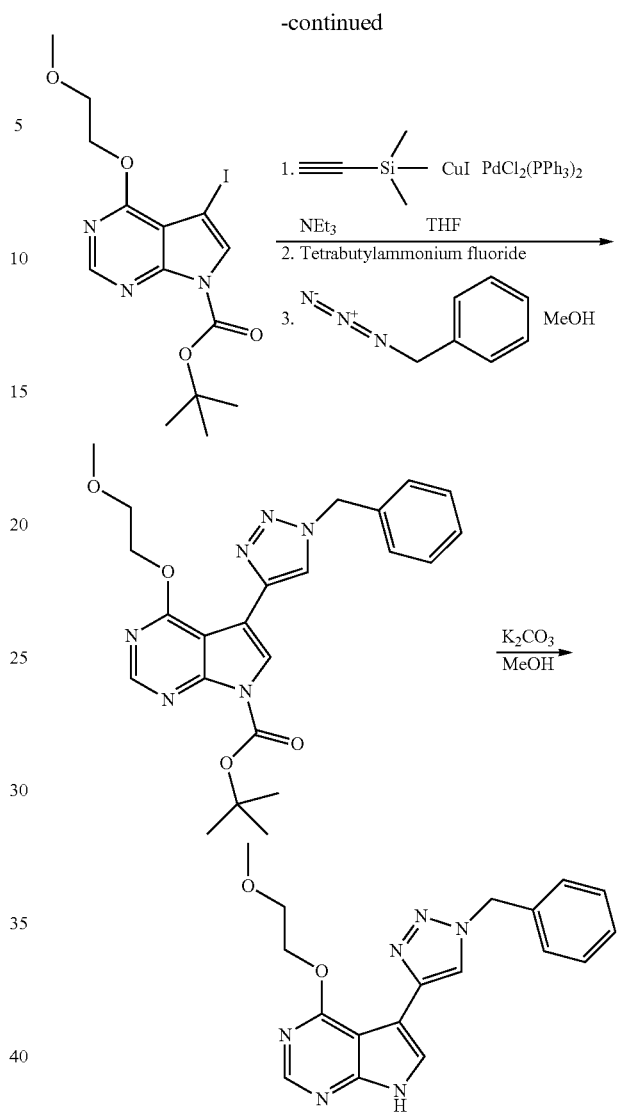

1.1 A suspension of 1.00 g (6.32 mmol) of 4-chloro-7H-pyrrolo[2,3-d]-pyrimidine and 5.20 g (15.8 mmol) of caesium carbonate in 30 ml of 2-methoxy-ethanol is heated under reflux for 24 hours. The reaction mixture is adsorbed onto kieselguhr and chromatographed on a silica-gel column with dichloromethane/methanol/aqueous ammonia (100:1:1) as eluent, giving 4-(2-methoxyethoxy)-7H-pyrrolo[2,3-d]pyrimidine as colourless crystals; m.p. 137-139° C.;

$^1$H-NMR (500 MHz, DMSO-d$_6$): δ [ppm]=3.30 (d, J=0.9 Hz, 3H), 3.70-3.73 (m, 2H), 4.57-4.61 (m, 2H), 6.46-6.48 (m, 1H), 7.33-7.36 (m, 1H), 8.35 (d, J=0.6 Hz, 1H), 12.0 (bs, 1H).

1.2 A solution of 1.28 g (5.05 mmol) of iodine in 10 ml of DMF is added dropwise to a mixture of 966 mg (5.00 mmol) of 4-(2-methoxyethoxy)-7H-pyrrolo[2,3-d]pyrimidine and 825 mg (12.5 mmol) of solid potassium hydroxide in 10 ml of DMF, and the mixture is subsequently stirred at room temperature for 50 minutes. The reaction mixture is poured into 100 ml of ice-water (containing 0.5% by weight of ammonia and 0.1% by weight of sodium disulfite) and left at 5° C. for 15 minutes. The precipitate formed is filtered off with suction, washed with 100 ml of ice-water and dried in vacuo: 5-iodo-4-(2-methoxyethoxy)-7H-pyrrolo[2,3-d]pyrimidine as yellow solid.

1.3 49 mg (0.40 mmol) of 4-dimethylaminopyridine are added to a suspension of 1.33 g (4.15 mmol) of 5-iodo-4-(2-methoxyethoxy)-7H-pyrrolo[2,3-d]pyrimidine in 8 ml of dichloromethane, and a solution of 1.33 g (5.93 mmol) of di-tert-butyl dicarbonate in 8 ml of dichloromethane is then added dropwise over the course of 20 minutes. The mixture is stirred at room temperature for 30 minutes, washed with 85 ml of 0.1 N aqueous hydrochloric acid, and the aqueous phase is extracted twice with dichloromethane. The combined organic phases are dried over sodium sulfate and evaporated. The residue is chromatographed on a silica-gel column with petroleum ether/ethyl acetate as eluent: tert-butyl 5-iodo-4-(2-methoxyethoxy)pyrrolo[2,3-d]pyrimidine-7-carboxylate as pale-yellow oil;

$^1$H-NMR (500 MHz, CDCl$_3$): δ [ppm]=1.67 (s, 9H), 3.49 (s, 3H), 3.84-3.88 (m, 2H), 4.67-4.71 (m, 2H), 7.62 (s, 1H), 8.62 (s, 1H).

1.4 0.37 ml (2.58 mmol) of trimethylsilylacetylene and 0.48 ml (3.44 mmol) of triethylamine are added successively to a suspension, kept under argon, of 24 mg (0.03 mmol) of bis(triphenylphosphine)palladium dichloride, 13 mg (0.07 mmol) of copper(I) iodide and 720 mg (1.72 mmol) of tert-butyl 5-iodo-4-(2-methoxyethoxy)-pyrrolo[2,3-d]pyrimidine-7-carboxylate in 9 ml of THF, and the mixture is stirred at room temperature for one hour under argon. 2.58 ml (2.58 mmol) of a 1 M solution of tetrabutylammonium fluoride in THF are then added, and the reaction mixture is stirred at room temperature for 30 minutes. A solution of 234 mg (1.782 mmol) of benzyl azide in 9 ml of methanol is then added, and the reaction mixture is stirred at room temperature for 87 hours. The reaction mixture is adsorbed onto kieselguhr and chromatographed on a silica-gel column with petroleum ether/ethyl acetate 1:1 as eluent: tert-butyl 5-(1-benzyl-1H-1,2,3-triazol-4-yl)-4-(2-methoxyethoxy)-pyrrolo[2,3-d]pyrimidine-7-carboxylate as pale-yellow foam.

1.5 195 mg (1.40 mmol) of potassium carbonate are added to a solution of 197 mg (0.56 mmol) of tert-butyl 5-(1-benzyl-1H-1,2,3-triazol-4-yl)-4-(2-methoxy-ethoxy)pyrrolo[2,3-d]pyrimidine-7-carboxylate in 2.8 ml of methanol, and the mixture is stirred at room temperature for 1 hour. The reaction mixture is adsorbed onto kieselguhr and chromatographed on a silica-gel column with dichloromethane/methanol/ammonia water as eluent: 5-(1-benzyl-1H-1,2,3-triazol-4-yl)-4-(2-methoxyethoxy)-7H-pyrrolo[2,3-d]pyrimidine ("A1") as colourless crystals; m.p. 240° C.;

$^1$H-NMR (500 MHz, DMSO-d$_6$): δ [ppm]=3.23 (s, 3H), 3.68-3.71 (m, 2H), 4.57-4.60 (m, 2H), 5.65 (s, 2H), 7.29-7.36 (m, 3H), 7.37-7.42 (m, 2H), 7.85 (s, 1H), 8.37 (s, 1H), 8.43 (s, 1H), 12.3 (bs, 1H).

The following compounds are obtained analogously

| No. | Name/structure |
|---|---|
| "A2" | 5-(1-Benzyl-1H-1,2,3-triazol-4-yl)-4-methoxy-7H-pyrrolo[2,3-d]pyrimidine |
| | HPLC/MS Rt. 1.86 min; |
| | HPLC/MS 307 [M + H]$^+$; $^1$H NMR (400 MHz, DMSO-d$_6$) δ [ppm] 12.25 (s, 1H), 8.38 (s, 1H), 8.34 (s, 1H), 7.78 (s, 1H), 7.38 (m, 5H), 5.67 (s, 2H), 4.05 (s, 3H) |
| "A3" | 5-[1-(3-Fluorobenzyl)-1H-1,2,3-triazol-4-yl]-4-(2-methoxyethoxy)-7H-pyrrolo[2,3-d]pyrimidine |
| "A4" | (3-{4-[4-(2-Methoxyethoxy)-7H-pyrrolo[2,3-d]-pyrimidin-5-yl]-1,2,3-triazol-1-yl}-3-phenylpropyl)-dimethylamine |
| "A5" | 5-[1-(3-Azetidin-1-yl-1-phenylpropyl)-1H-1,2,3-triazol-4-yl]-4-(2-methoxyethoxy)-7H-pyrrolo[2,3-d]-pyrimidine |

Example 2

Preparation of 5-(1-benzyl-1H-1,2,3-triazol-4-yl)-7H-pyrrolo[2,3-d]pyrimidine ("A6")

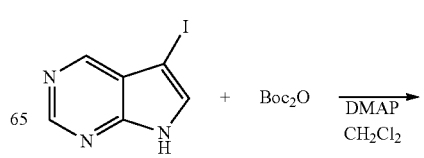

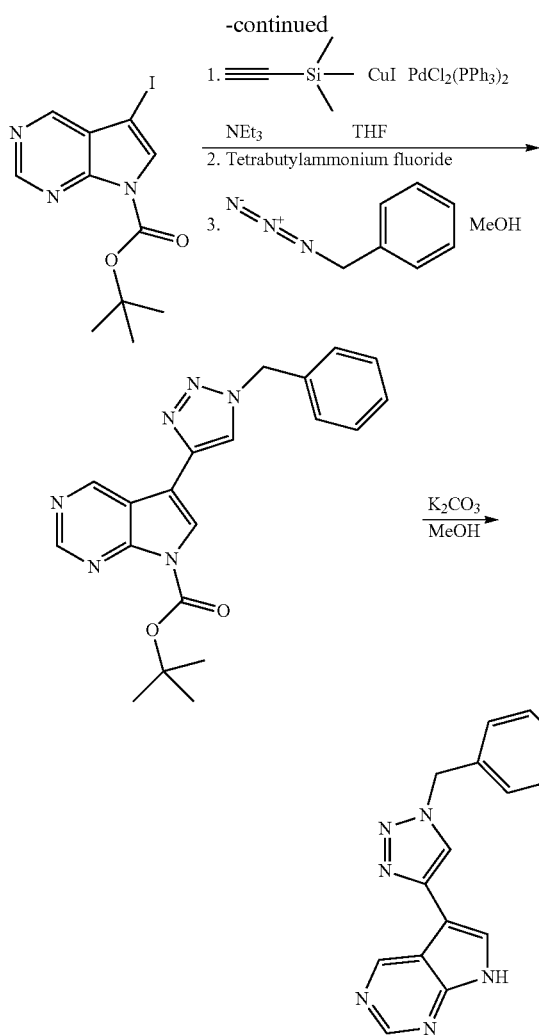

2.1 10 ml (7.1 mmol) of triethylamine and 379 mg (3.10 mmol) of 4-(dimethylamino)pyridine are added successively to a suspension of 7.60 g (31.0 mmol) of 5-iodo-7H-pyrrolo[2,3-d]pyrimidine (synthesis described in WO 2009/080682) in 200 ml of dichloromethane. A solution of 7.30 ml (34.0 mmol) of di-tert-butyl dicarbonate in 200 ml of dichloromethane is added dropwise thereto at room temperature with stirring. After stirring at room temperature for one hour, the reaction mixture is extracted three times with water. The organic phase is dried over sodium sulfate and evaporated, giving tert-butyl 5-iodopyrrolo[2,3-d]pyrimidine-7-carboxylate as yellow solid; HPLC/MS: 2.26 min, [M+H] 346.

2.2 361 µl (2.61 mmol) of trimethylsilylacetylene and 402 µl (2.90 mmol) of triethylamine were added to a suspension, kept under nitrogen, of 500 mg (1.45 mmol) of tert-butyl 5-iodopyrrolo[2,3-d]pyrimidine-7-carboxylate, 19.5 mg (0.028 mmol) of bis(triphenylphosphine)palladium(II) chloride and 11.2 mg (0.059 mmol) of copper(I) iodide in 5 ml of THF, and the mixture was stirred at room temperature for 18 hours. Nitrogen was then passed through the reaction mixture for 10 minutes, and 4.4 ml of a 1 M solution of tetrabutylammonium fluoride in THF were subsequently added. After stirring at room temperature for three hours, 309 mg (2.32 mmol) of benzyl azide were added, and the reaction mixture was stirred at room temperature for 40 hours under nitrogen. The reaction mixture was partitioned between water and ethyl acetate. The organic phase was dried over sodium sulfate and evaporated. The residue was purified by preparative HPLC, giving tert-butyl 5-(1-benzyl-1H-1,2,3-triazol-4-yl)pyrrolo[2,3-d]pyrimidine-7-carboxylate as colourless solid; HPLC/MS: 2.23 min, [M+H] 377.

17 mg (0.13 mmol) of potassium carbonate were added to a solution of 13 mg (0.035 mmol) of tert-butyl 5-(1-benzyl-1H-1,2,3-triazol-4-yl)pyrrolo[2,3-d]pyrimidine-7-carboxylate in 10 ml of methanol, and the mixture was stirred at room temperature for 18 hours. The reaction mixture was evaporated, and the residue was purified by preparative HPLC, giving 5-(1-benzyl-1H-1,2,3-triazol-4-yl)-7H-pyrrolo[2,3-d]pyrimidine as colourless solid; HPLC/MS: 1.48 min, [M+H] 277;

$^1$H NMR (400 MHz, DMSO-$d_6$) δ [ppm] 12.31 (s, 1H), 9.44 (s, 1H), 8.81 (s, 1H), 8.59 (s, 1H), 7.98 (d, J=2.5, 1H), 7.38 (m, 5H), 5.66 (s, 2H).

"A7" and "A8" are prepared analogously, starting from 5-iodo-2-methoxy-7H-pyrrolo[2,3-d]pyrimidine and 5-iodo-2,4-dimethoxy-7H-pyrrolo[2,3-d]pyrimidine respectively (both commercially available).

| No. | Name/structure |
|---|---|
| "A7" | 5-(1-Benzyl-1H-1,2,3-triazol-4-yl)-2-methoxy-7H-pyrrolo[2,3-d]pyrimidine |
| "A8" | 5-(1-Benzyl-1H-1,2,3-triazol-4-yl)-2,4-dimethoxy-7H-pyrrolo[2,3-d]pyrimidine |

Example 3

Synthesis of 1-(3-azido-3-phenylpropyl)azetidine (for the preparation of "A5")

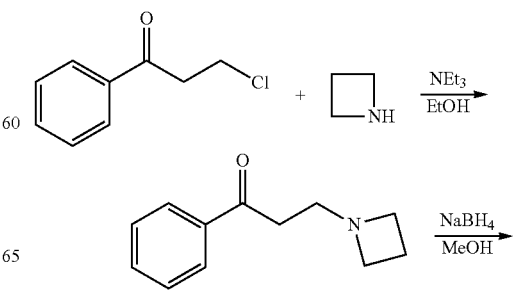

-continued

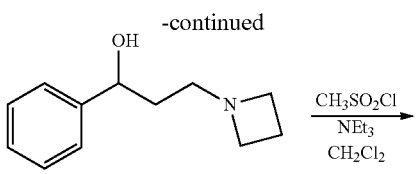

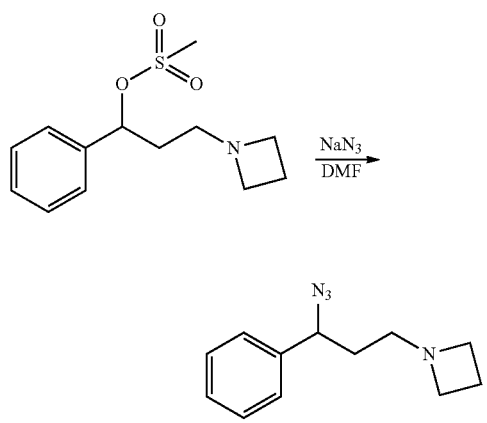

3.1 1.85 ml of triethylamine and 440 µl (6.55 mmol) of azetidine are added to a solution of 1.00 g (5.93 mmol) of 3-chloro-1-phenylpropan-1-one in ethanol, and the mixture is stirred at RT for 4 hours. The reaction mixture is partitioned between water and saturated sodium chloride solution. The organic phase is dried over sodium sulfate and evaporated: 3-azetidin-1-yl-1-phenyl-propan-1-one as colourless oil; HPLC/MS 0.7 min; [M+H] 190.

3.2 1.60 g (42.3 mmol) of sodium borohydride are added in portions to a solution, kept at 0° C., of 2.76 g (13.7 mmol) of 3-azetidin-1-yl-1-phenylpropan-1-one in 50 ml of methanol), and the mixture is stirred at RT for 3 h. Water is added, the methanol is removed in vacuo, and the residue is taken up using ethyl acetate. The mixture is washed three times with water and once with saturated sodium chloride solution, dried over sodium sulfate and evaporated: 3-azetidin-1-yl-1-phenylpropan-1-ol as viscous oil; HPLC/MS 0.7 min; [M+H] 192.

3.3 A solution of 1.12 ml (14.30 mmol) of methanesulfonyl chloride in 5 ml of dichloromethane is added dropwise to a solution of 2.49 g (13.0 mmol) of 3-azetidin-1-yl-1-phenyl-propan-1-ol and 2.70 ml (19.5 mmol) of triethylamine in 65 ml of dichloromethane, and the reaction mixture is stirred at room temperature for 3 hours. The reaction mixture is washed three times with water, dried over sodium sulfate and evaporated to dryness: 3-azetidin-1-yl-1-phenylpropyl methanesulfonate as viscous oil, which was employed for the following reaction without further purification.

3.4 1.50 g (23.1 mmol) of sodium azide are added to a solution of 2.00 g (7.43 mmol) of 3-azetidin-1-yl-1-phenyl-propyl methanesulfonate in 50 ml of DMF, and the mixture is stirred at room temperature for 48 hours. The reaction mixture is partitioned between water and ethyl acetate. The organic phase is dried over sodium sulfate, evaporated, and the residue is chromatographed on a silica-gel column with ethyl acetate/methanol as eluent: 1-(3-azido-3-phenyl-propyl)azetidine as colourless viscous oil; HPLC/MS 0.9 min; [M+H] 217.

The azide derivative required for "A4" is prepared analogously.

Example 4

Synthesis of 5-{1-[1-(2,3-difluorophenyl)-3-piperidin-1-ylpropyl]-1H-1,2,3-triazol-4-yl}-7H-pyrrolo[2,3-d]pyrimidine ("A9")

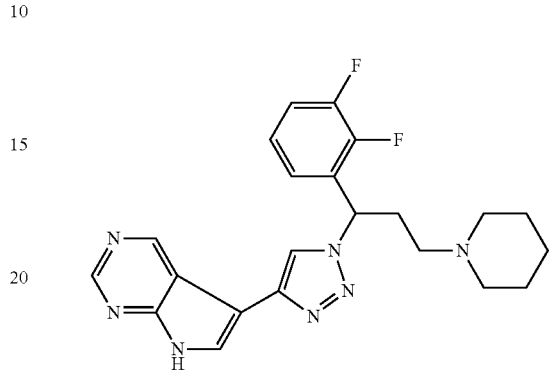

The preparation is carried out analogously to Example 1; the azide required for this purpose is prepared analogously to Example 3; "A9" is obtained as trifluoroacetate.
HPLC/MS Rt. 1.27 min;
HPLC/MS 424 [M+H]$^+$;
$^1$H NMR (400 MHz, DMSO-d$_6$) δ [ppm] 12.6 (s, 1H), 9.49 (s, 1H), 9.20 (s, 1H), 8.90 (s, 1H), 8.72 (s, 1H), 8.07 (d, J=2.3, 1H), 7.51 (ddd, J=18.1, 7.7, 2.3, 1H), 7.33 (m, 2H), 6.27 (dd, J=8.7, 5.8, 1H), 3.20 (m, 2H), 2.98 (m, 4H), 2.70 (m, 2H), 1.80 (m, 2H), 1.64 (m, 3H), 1.38 (m, 1H).

Inhibition of PDK1, TBK1 and IKK
IC$_{50}$ of compounds according to the invention

| Compound No. | IC$_{50}$ PDK1 | IC$_{50}$ TBK1 | IC$_{50}$ IKK |
|---|---|---|---|
| "A1" | A | A | B |
| "A2" | A | A | A |
| "A3" | | | |
| "A6" | B | B | B |
| "A9" | B | C | B |

IC$_{50}$:
10 nM-1M = A
1M-10M = B
>10M = C

Vitality Assay
IC$_{50}$ of compounds according to the invention

| Compound No. | IC$_{50}$ A2780 | IC$_{50}$ HCT 116 |
|---|---|---|
| "A1" | B | B |

IC$_{50}$:
10 nM-1M = A
1M-10M = B

The following examples relate to medicaments:

Example A

Injection Vials

A solution of 100 g of an active compound of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

Example B

Suppositories

A mixture of 20 g of an active compound of the formula I with 100 g of soya lecithin and 1400 g of cocoa butter is melted, poured into moulds and allowed to cool. Each suppository contains 20 mg of active compound.

Example C

Solution

A solution is prepared from 1 g of an active compound of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active compound of the formula I are mixed with 99.5 g of Vaseline under aseptic conditions.

Example E

Tablets

A mixture of 1 kg of active compound of the formula I, 4 kg of lactose, 1.2 kg of potato starch, 0.2 kg of talc and 0.1 kg of magnesium stearate is pressed in a conventional manner to give tablets in such a way that each tablet contains 10 mg of active compound.

Example F

Dragees

Tablets are pressed analogously to Example E and subsequently coated in a conventional manner with a coating of sucrose, potato starch, talc, tragacanth and dye.

Example G

Capsules 2 kg of active compound of the formula I are introduced into hard gelatine capsules in a conventional manner in such a way that each capsule contains 20 mg of the active compound.

Example H

Ampoules

A solution of 1 kg of active compound of the formula I in 60 l of bidistilled water is sterile filtered, transferred into ampoules, lyophilised under sterile conditions and sealed under sterile conditions. Each ampoule contains 10 mg of active compound.

The invention claimed is:
1. A compound of the formula I

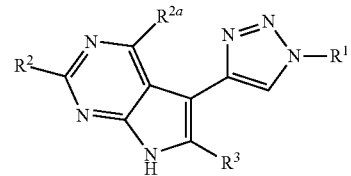

in which
$R^1$ denotes A, —$C(R^3)(R^4)$—Ar, —$C(R^3)(R^4)$-Het or —$C(R^3)(R^4)$-Cyc,
$R^2$, $R^{2a}$ each, independently of one another, denote H, A, Hal, CN, —$[C(R^3)_2]_n$—Ar', —$[C(R^3)_2]_n$-Het', —$[C(R^3)_2]_n$-Cyc, $OR^3$ or $N(R^3)_2$,
$R^3$ denotes H,
$R^4$ denotes H, A, —$[C(R^3)_2]_mOR^3$, —$[C(R^3)_2]_mN(R^3)_2$ or —$[C(R^3)_2]_mHet^1$,
A denotes unbranched or branched alkyl having 1-6 C atoms, in which one or two non-adjacent $CH_2$ groups may be replaced by O, N and/or S atoms and/or by —CH=CH— groups and/or, in addition, 1-7 H atoms may be replaced by F,
Cyc denotes cycloalkyl having 3, 4, 5, 6 or 7 C atoms,
Ar denotes phenyl which is unsubstituted or mono-, di- or trisubstituted by Hal, A, $OR^3$, $N(R^3)_2$, $NO_2$, CN, $COOR^3$, $CON(R^3)_2$, $NR^3COA$, $NR^3SO_2A$, $COR^3$, $SO_2N(R^3)_2$ and/or $S(O)_nA$,
Ar' denotes phenyl which is unsubstituted or mono-, di- or trisubstituted by Hal, A, $OR^3$, $N(R^3)_2$, $SR^3$, $NO_2$, CN, $COOR^3$, $CON(R^3)_2$, $NR^3COA$, $NR^3SO_2A$, $SO_2N(R^3)_2$, $S(O)_mA$, CO-$Het^1$, $Het^1$, $[C(R^3)_2]_nN(R^3)_2$, $[C(R^3)_2]_nHet^1$, $O[C(R^3)_2]_nN(R^3)_2$, $O[C(R^3)_2]_nHet^1$, NHCOOA, $NHCON(R^3)_2$, $NHCOO[C(R^3)_2]_nN(R^3)_2$, NHCOO[C$(R^3)_2]_n$Het$^1$, NHCONH[C$(R^3)_2]_n$N$(R^3)_2$, NHCONH[C$(R^3)_2]_1$Het$^1$, OCONH[C$(R^3)_2]_n$N$(R^3)_2$, OCONH[C$(R^3)_2]_n$Het$^1$, CO-$Het^1$, CHO and/or COA,
Het denotes a mono- or bicyclic saturated, unsaturated or aromatic heterocycle having 1 to 4 N, and/or O and/or S atoms which is unsubstituted or mono- or disubstituted by Hal, A, $OR^3$, $N(R^3)_2$, $NO_2$, CN, $COOR^3$, $CON(R^3)_2$, $NR^3COA$, $NR^3SO_2A$, $COR^3$, $SO_2NR^3$ and/or $S(O)_nA$,
Het' denotes a mono-, bi- or tricyclic saturated, unsaturated or aromatic heterocycle having 1 to 4 N, O and/or S atoms, which is unsubstituted or may be mono- or disubstituted by Hal, A, $OR^3$, $N(R^3)_2$, $SR^3$, $NO_2$, CN, $COOR^3$, $CON(R^3)_2$, $NR^3COA$, $NR^3SO_2A$, $SO_2N(R^3)_2$, $S(O)_mA$, CO-$Het^1$, $Het^1$, $[C(R^3)_2]_nN(R^3)_2$, $[C(R^3)_2]_nHet^1$, $O[C(R^3)_2]_nN(R^3)_2$, $O[C(R^3)_2]_nHet^1$, NHCOOA, $NHCON(R^3)_2$, $NHCOO[C(R^3)_2]_nN(R^3)_2$, NHCOO[C$(R^3)_2]_n$Het$^1$, NHCONH[C$(R^3)_2]_1$N$(R^3)_2$, NHCONH[C$(R^3)_2]_n$Het$^1$, OCONH[C$(R^3)_2]_n$N$(R^3)_2$, OCONH[C$(R^3)_2]_n$-Het$^1$, CO-$Het^1$, CHO, COA, =S, =NH, =NA and/or =O (carbonyl oxygen),
Het$^1$ denotes a monocyclic saturated heterocycle having 1 to 2 N and/or O atoms, which may be mono- or disubstituted by A, OA, OH, Hal and/or =O (carbonyl oxygen),
Hal denotes F, Cl, Br or I
N denotes 0, 1 or 2 m denotes 1 or 2,
or a pharmaceutically usable salt, tautomer or stereoisomer thereof, including mixtures thereof in all ratios.

2. A compound according to claim 1 in which
R¹ denotes —C(R³)(R⁴)—Ar,
or a pharmaceutically usable salt, tautomer or stereoisomer thereof, including mixtures thereof in all ratios.

3. A compound according to claim 1 in which
R², R²ᵃ each, independently of one another, denotes H or A,
or a pharmaceutically usable salt, tautomer or stereoisomer thereof, including mixtures thereof in all ratios.

4. A compound according to claim 1 in which
R⁴ denotes H, —[C(R³)₂]ₘN(R³)₂ or —[C(R³)₂]ₘHet¹,
or a pharmaceutically usable salt, tautomer or stereoisomer thereof, including mixtures thereof in all ratios.

5. A compound according to claim 1 in which
A denotes unbranched or branched alkyl having 1-6 C atoms, in which one or two non-adjacent CH₂ groups may be replaced by an O, N and/or S atom and/or, in addition, 1-7 H atoms may be replaced by F,
or a pharmaceutically usable salt, tautomer or stereoisomer thereof, including mixtures thereof in all ratios.

6. A compound according to claim 1 in which
Ar denotes phenyl which is unsubstituted or mono- or disubstituted by Hal and/or A,
or a pharmaceutically usable salt, tautomer or stereoisomer thereof, including mixtures thereof in all ratios.

7. A compound according to claim 1 in which
Het¹ denotes a monocyclic saturated heterocycle having 1 to 2 N and/or O atoms, which may be mono- or disubstituted by A,
or a pharmaceutically usable salt, tautomer or stereoisomer thereof, including mixtures thereof in all ratios.

8. A compound according to claim 1 in which
Het¹ denotes azetidinyl, pyrrolidinyl, tetrahydroimidazolyl, tetrahydropyrazolyl, piperidinyl, morpholinyl, piperazinyl, oxazolidinyl or isoxazolidinyl, each of which is unsubstituted or mono- or disubstituted by A,
or a pharmaceutically usable salt, tautomer or stereoisomer thereof, including mixtures thereof in all ratios.

9. A compound according to claim 1 in which
R¹ denotes —C(R³)(R⁴)—Ar,
R², R²ᵃ each, independently of one another, denote H or A,
R³ denotes H,
R⁴ denotes H, —[C(R³)₂]ₘN(R³)₂ or —[C(R³)₂]ₘHet¹,
A denotes unbranched or branched alkyl having 1-6 C atoms, in which one or two non-adjacent CH₂ groups may be replaced by an O, N and/or S atom and/or, in addition, 1-7 H atoms may be replaced by F,
Ar denotes phenyl which is unsubstituted or mono- or disubstituted by Hal and/or A,
Het¹ denotes a monocyclic saturated heterocycle having 1 to 2 N and/or O atoms, which may be once or twice by A,
Hal denotes F, Cl, Br or I,
M denotes 1 or 2,
or a pharmaceutically usable salt, tautomer or stereoisomer thereof, including mixtures thereof in all ratios.

10. A compound according to claim 1, selected from the following compounds:

| Compound No. | Name and/or structure |
|---|---|
| "A1" | 5-(1-Benzyl-1H-1,2,3-triazol-4-yl)-4-(2-methoxyethoxy)-7H-pyrrolo[2,3-d]pyrimidine |
| "A2" | 5-(1-Benzyl-1H-1,2,3-triazol-4-yl)-4-methoxy-7H-pyrrolo[2,3-d]pyrimidine |
| "A3" | 5-[1-(3-Fluorobenzyl)-1H-1,2,3-triazol-4-yl]-4-(2-methoxyethoxy)-7H-pyrrolo[2,3-d]pyrimidine |
| "A4" | (3-{4-[4-(2-Methoxyethoxy)-7H-pyrrolo[2,3-d]-pyrimidin-5-yl]-1,2,3-triazol-1-yl}-3-phenylpropyl)-dimethylamine |
| "A5" | 5-[1-(3-Azetidin-1-yl-1-phenylpropyl)-1H-1,2,3-triazol-4-yl]-4-(2-methoxyethoxy)-7H-pyrrolo[2-3-d]-pyrimidine |
| "A6" | 5-(1-Benzyl-1H-1,2,3-triazol-4-yl)-7H-pyrrolo[2,3-d]-pyrimidine |
| "A7" | 5-(1-Benzyl-1H-1,2,3-triazol-4-yl)-2-methoxy-7H-pyrrolo[2,3-d]pyrimidine |
| "A8" | 5-(1-Benzyl-1H-1,2,3-triazol-4-yl)-2,4-dimethoxy-7H-pyrrolo[2,3-d]pyrimidine |
| "A9" | 5-{1-[1-(2,3-Difluorophenyl)-3-piperidin-1-yl-propyl]-1H-1,2,3-triazol-4-yl}-7H-pyrrolo[2,3-d]pyrimidine | or a pharmaceutically usable salt, tautomer or stereoisomer thereof, including mixtures thereof in all ratios.

11. A process for the preparation of a compound of the formula I according to claim 1 or a pharmaceutically usable salt, tautomer or stereoisomer thereof, comprising:

cleaving off an indole-protecting group from a compound of the formula II

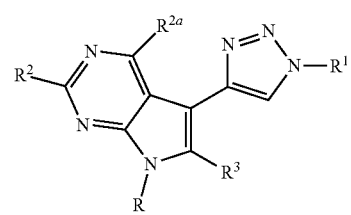

in which R¹, R², R²ᵃ and R³ have the meanings indicated in claim 1 and R denotes the indole-protecting group, and/or converting a base or acid of the formula I into one of its salts.

12. A medicament composition comprising ing at least one compound of the formula I according to claim 1 or a pharmaceutically usable salt, tautomer or stereoisomer thereof, including mixtures thereof in all ratios, and optionally excipients and/or adjuvants.

13. A method for inhibiting PDK-1 in vitro, which comprises contacting a compound according to claim 1 or a pharmaceutically usable salt, tautomer or stereoisomer thereof, including mixtures thereof in all ratios, with PDK-1.

* * * * *